(12) United States Patent
Omoda et al.

(10) Patent No.: US 9,276,301 B2
(45) Date of Patent: Mar. 1, 2016

(54) POLYMERIC COMPOUND, OXYGEN PERMEABLE MEMBRANE, AND ELECTROCHEMICAL DEVICE

(71) Applicant: Samsung Electronics Co., Ltd., Suwon-si, Gyeonggi-do (KR)

(72) Inventors: Ryo Omoda, Kanagawa (JP); Hiroyuki Nishide, Kanagawa (JP); Satoshi Nakajima, Kanagawa (JP); Yuichi Aihara, Kanagawa (JP)

(73) Assignee: SAMSUNG ELECTRONICS CO., LTD. (KR)

( * ) Notice: Subject to any disclaimer, the term of this patent is extended or adjusted under 35 U.S.C. 154(b) by 87 days.

(21) Appl. No.: 14/098,609

(22) Filed: Dec. 6, 2013

(65) Prior Publication Data

US 2014/0162148 A1    Jun. 12, 2014

(30) Foreign Application Priority Data

Dec. 7, 2012    (JP) ................................. 2012-268869
Aug. 20, 2013    (KR) ........................ 10-2013-0098613

(51) Int. Cl.
*H01M 12/08*    (2006.01)
*C07D 487/22*    (2006.01)

(52) U.S. Cl.
CPC ............. *H01M 12/08* (2013.01); *C07D 487/22* (2013.01); *Y02E 60/50* (2013.01)

(58) Field of Classification Search
CPC ..... H01M 12/08; H01M 4/8605; Y02E 60/50
See application file for complete search history.

(56) References Cited

U.S. PATENT DOCUMENTS

| | | | |
|---|---|---|---|
| 5,147,424 A * | 9/1992 | Tsuchida et al. | 96/14 |
| 5,955,603 A | 9/1999 | Therien et al. | |
| 5,985,475 A | 11/1999 | Reynolds et al. | |
| 6,515,089 B1 * | 2/2003 | Asano et al. | 526/259 |
| 8,906,562 B2 * | 12/2014 | Nishide et al. | 429/403 |
| 2003/0157386 A1 | 8/2003 | Gottmann et al. | |
| 2009/0314660 A1 | 12/2009 | Canonne et al. | |
| 2010/0203397 A1 | 8/2010 | Thiemann-Handler et al. | |
| 2014/0141343 A1 * | 5/2014 | Nishide et al. | 429/407 |

FOREIGN PATENT DOCUMENTS

| | | | |
|---|---|---|---|
| CN | 102977403 | * | 3/2013 |
| JP | 57-111957 A | | 7/1982 |
| JP | S59221971 A | * | 12/1984 |

(Continued)

OTHER PUBLICATIONS

Aota, H., et al. "New Polymers Containing Pendant Metalloporphyrins. Radical Polymerization of 2-Acryloyloxymethylene5,1 0, 15,20-tetraphenylporphinatometals," Chemistry Letters. pp. 823-826. 1990.*

(Continued)

*Primary Examiner* — Liam J Heincer
*Assistant Examiner* — Nicholas Hill
(74) *Attorney, Agent, or Firm* — Cantor Colburn LLP

(57) ABSTRACT

A polymeric compound including a cross-linked backbone which is a product of a reaction between a multifunctional acrylate compound and a metal porphyrin derivative, wherein the metal porphyrin derivative has a first axial position and a second axial position, and further includes a basic coordination ligand coordinated at the first axial position of the metal porphyrin derivative.

19 Claims, 3 Drawing Sheets

(56) References Cited

FOREIGN PATENT DOCUMENTS

| | | |
|---|---|---|
| JP | 05-261851 A | 10/1993 |
| JP | 05-326035 A | 12/1993 |
| JP | 05-326036 A | 12/1993 |
| JP | 05-326037 A | 12/1993 |
| JP | 08-007935 A | 1/1996 |
| JP | 09-274936 A | 10/1997 |
| JP | 09-289045 A | 11/1997 |
| JP | 10-064603 A | 3/1998 |
| JP | 2000-106154 A | 4/2000 |
| JP | 2002-503151 A | 1/2002 |
| JP | 2002-177747 A | 6/2002 |
| JP | 2003-017143 A | 1/2003 |
| JP | 2003-036895 A | 2/2003 |
| JP | 2003-053125 A | 2/2003 |
| JP | 2003-297440 A | 10/2003 |
| JP | 2004-288572 A | 10/2004 |
| JP | 2004-319464 A | 11/2004 |
| JP | 2005-518643 A | 6/2005 |
| JP | 2005-294107 A | 10/2005 |
| JP | 2006-142275 A | 6/2006 |
| JP | 2007-141745 A | 6/2007 |
| JP | 2008-059821 A | 3/2008 |
| JP | 2009-515002 A | 4/2009 |
| JP | 2009-099570 A | 5/2009 |
| JP | 2009-230981 A | 10/2009 |
| JP | 2010-056070 A | 3/2010 |
| JP | 2010-0528412 A | 8/2010 |
| JP | 2011-086610 A | 4/2011 |
| JP | 2011-113719 A | 6/2011 |
| JP | 2011-119189 A | 6/2011 |
| JP | 2011-171260 A | 9/2011 |
| JP | 2012-015016 A | 1/2012 |
| JP | 2013-033721 A | 2/2013 |
| JP | 2013129705 * | 7/2013 |
| KR | 1020130071362 * | 6/2013 |
| KR | 1020130071362 A | 6/2013 |
| WO | 9858418 A1 | 12/1998 |

OTHER PUBLICATIONS

Natsuru Chikushi, et al., "Porphyrin Network Polymers Prepared via a Click Reaction and Facilitated Oxygen Permeation Through Their Membranes," Macromol. Rapid Commun. 2014, 35, 976-980.*

Makoto Obata, et al., "Oxygen-Sensing Properties of 5,10,15,20-Tetraphenylporphinato Platinum(II) and Palladium(II) Covalently Bound on Poly(isobutyl-co-2,2,2-trifluoroethyl methacrylate)," Journal of Polymer Science: Part A: Polymer Chemistry, vol. 48, 663-670 (2010).*

Fumie Takei, et al., "Precise Synthesis of Porphyrin Array Scaffolding Polyisocyanides," Journal of Polymer Science: Part A: Polymer Chemistry, vol. 44, 585-595 (2006).*

* cited by examiner

POLYMERIC COMPOUND, OXYGEN PERMEABLE MEMBRANE, AND ELECTROCHEMICAL DEVICE

CROSS-REFERENCE TO RELATED APPLICATION

This application claims the benefit of Japanese Patent Application No. 2012-268869, filed on Dec. 7, 2012 and Korean Patent Application No. 10-2013-0098613, filed on Aug. 20, 2013, and all the benefits accruing therefrom under 35 U.S.C. §119, the contents of which are incorporated herein in its entirety by reference.

BACKGROUND

1. Field

The present disclosure relates to a method and an apparatus for preparing a polymeric compound that selectively intercalate and deintercalate oxygen, oxygen-permeable membranes including the polymeric compound, and an electrochemical device using the oxygen-permeable membrane.

2. Description of the Related Art

Recently, electrochemical devices, such as rechargeable secondary batteries using oxygen as a positive active material, for example, lithium air batteries, have drawn attention. In such electrochemical devices, oxygen is externally supplied (from the air or an external oxygen supply unit) in a discharging operation, which is then involved in oxidation reduction reactions in electrodes during charging and discharging operations. Thus, in electrochemical devices, such as lithium air batteries using oxygen in a redox reaction, for example, a lithium air battery, rapid and efficient introduction of oxygen into the device is becoming an important issue in view of electrical capacity maximization. In particular, because oxygen in the air is supplied into an electrochemical device, an efficient way to introduce oxygen from the air, including other components, such as nitrogen, is desired. To this end, a member capable of selectively binding (intercalation/deintercalation) to oxygen molecules may be disposed at an oxygen inlet near a positive electrode (air electrode) of an electrochemical device.

As a material capable of selectively binding oxygen, a cobalt porphyrin derivative of a core of a porphyrin molecule coordinated to cobalt is known. The cobalt porphyrin derivative has the same shape as hemoglobin and may selectively or reversibly bind an oxygen molecule through the permeation of oxygen. In a polymer membrane, in which the cobalt porphyrin derivative is included as an oxygen carrier, oxygen is selectively introduced into the polymer membrane and the oxygen moves rapidly therein. Accordingly, the polymer membrane including the cobalt porphyrin derivative may selectively enable permeation of oxygen, and as a consequence, more research is being conducted now than before focused on the industrial applicability of the polymer membrane as an oxygen selective permeable membrane or an oxygen enrichment membrane.

However, because the cobalt porphyrin derivative is a rigid molecule that lacks flexibility, a polymer backbone other than the porphyrin derivative or a polymer material separately mixed has to be used in large amount in a conventional membrane to achieve high workability and free-standing membrane property. Accordingly, a sufficient selective intercalation and deintercalation function of the cobalt porphyrin derivative and an oxygen permeability function of the membrane using the cobalt porphyrin derivative are difficult to achieve. Also, the membrane having the cobalt porphyrin derivative as a main material has a pressure difference before and after the formation of the membrane that is equal to or greater than oxygen partial pressure in the air and thus, the selective permeability of oxygen is low.

Accordingly, a demand for a polymeric compound having improved selective permeability of oxygen, an oxygen permeable membrane using the polymeric compound, and an electrochemical device using the oxygen permeable membrane still exist.

SUMMARY

Provided are polymeric compounds having improved oxygen selective permeability due to the improvement in selective oxygen permeability of a metal porphyrin derivative, despite a pressure difference that is equal to or greater than oxygen partial pressure in the air, oxygen permeable membranes using the polymeric compounds, and electrochemical devices having excellent performance by using the oxygen permeable membranes.

Additional aspects will be set forth in part in the description which follows and, in part, will be apparent from the description, or may be learned by practice of the presented embodiments.

According to an aspect of the present disclosure, provided is a polymeric compound including a cross-linked backbone which is a reaction product of a multifunctional acrylate compound and a metal porphyrin derivative, wherein the metal porphyrin derivative may have a first axial position and a second axial position, and may further include a basic coordination ligand coordinated at the first axial position of the metal porphyrin derivative.

The metal porphyrin derivative may further include an oxygen molecule coordinated at the second axial position of the metal porphyrin derivative.

The basic coordination ligand may include a nitrogen-containing organic ligand.

The metal porphyrin derivative may be a complex in which a metal is coordinated to a tetraphenylporphyrin derivative represented by Formula 1:

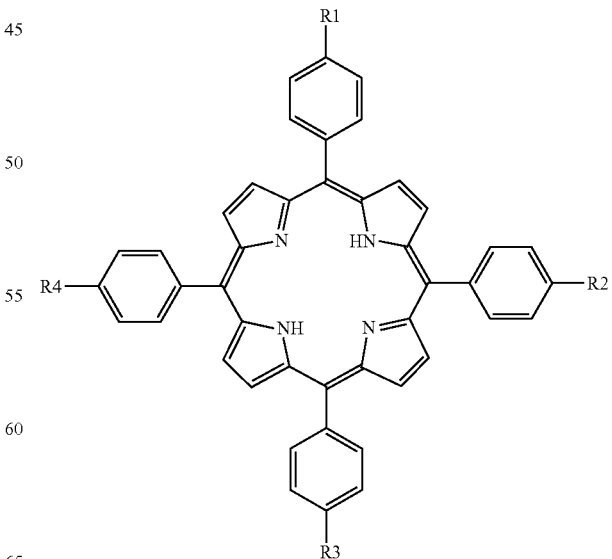

Formula 1 wherein in Formula 1 above,

R1, R2, R3, and R4 are each independently an acetoacetate group, an acetoacetamide group, a cyanoacetate group, a cyanoacetamide group, hydrogen, a halogen group, a substituted or unsubstituted C1-C10 alkyl group, a substituted or unsubstituted C2-C10 alkenyl group, a substituted or unsubstituted C2-C10 alkynyl group, a substituted or unsubstituted C6-C10 aryl group, or a combination thereof, wherein, at least one of R1, R2, R3, and R4 includes a group selected from an amino group, an acetoacetate group, an acetoacetamide group, a cyanoacetate group, and a cyanoacetamide group.

The polymeric compound may include the reaction product of the multifunctional acrylate compound and the metal porphyrin derivative may be a Michael-type addition reaction product.

The metal porphyrin derivative may include at least one nucleophilic group bound to an acryl group of the multifunctional acrylate compound to form a Michael-type addition reaction product.

A portion of the metal porphyrin derivative may be included in a main chain or a pendant group of the cross-linked backbone.

An amount of the metal porphyrin derivative may be 30 weight % or greater based on the weight of the polymeric compound.

The multifunctional acrylate compound may include a bifunctional acrylate, a trifunctional acrylate, or a tetrafunctional acrylate, or a combination thereof.

The multifunctional acrylate compound may be an acrylate compound comprising 20 or less carbon atoms.

The multifunctional acrylate compound may include a C1-C10 halogen-substituted alkylene group.

According to another aspect of the present disclosure, provided is an oxygen permeable membrane including the polymeric compound.

The oxygen permeable membrane may include an oxygen permeable composite membrane disposed on a porous substrate or in pores of the porous substrate.

The porous substrate may include a gas permeable polymer membrane disposed thereon.

The gas permeable polymer membrane may include poly(1-trimethylsilyl propene).

The oxygen permeable membrane may have a transmission coefficient of oxygen is at least 8 times greater than a transmission coefficient of nitrogen when a pressure difference of oxygen before and after the formation of the membrane is 1 centimeter of mercury, and the oxygen permeable membrane may have a transmission coefficient of oxygen at least 2 times greater than a transmission coefficient of nitrogen when a pressure difference of oxygen before and after the formation of the membrane is 50 centimeters of mercury.

According to another aspect of the present disclosure, provided is an electrochemical device including:
a positive electrode using oxygen as a positive active material,
a negative electrode using a material that intercalates and deintercalates lithium ions as
a negative active material,
an electrolyte disposed between the positive electrode and the negative electrode, and
a barrier formed of the oxygen permeable membrane described above, wherein the barrier is used as a medium for supplying oxygen to the positive electrode.

The electrochemical device may include the oxygen permeable membrane as described above.

The electrochemical device may be a lithium air battery. The negative active material may be a lithium metal.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
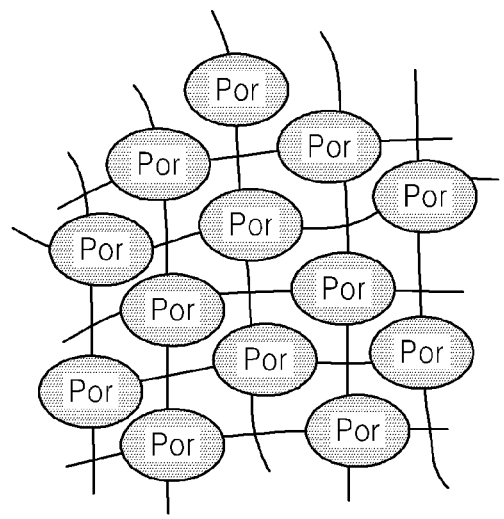
FIG. 1A is a conceptual diagram illustrating a structure of a polymeric compound according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As used herein, the term "alkyl group" indicates a completely saturated, branched or unbranched hydrocarbon group having the specified number of carbon atoms. Non-limiting examples of the "alkyl" group include methyl, ethyl, n-propyl, or i-propyl.

As used herein, the term "alkenyl group" indicates a branched or unbranched hydrocarbon group including at least one carbon-carbon double bond and having the specified number of carbon atoms. Non-limiting examples of the alkenyl group include vinyl, butenyl, i-propenyl, and i-butenyl.

As used herein, the term "alkynyl group" indicates a branched or unbranched hydrocarbon group including at least one carbon-carbon triple bond and having the specified number of carbon atoms. Non-limiting examples of the alkynyl group include ethynyl, propargyl, or 1-butynyl, or 2-butynyl.

As used herein, the term "aryl group" indicates an aromatic hydrocarbon group containing at least one ring and having the specified number of carbon atoms. The term "aryl" may be construed as including a group with an aromatic ring fused to at least one cycloalkyl ring. Non-limiting examples of the "aryl" group include phenyl, naphthyl, and tetrahydronaphthyl.

The term "halogen group" indicates fluorine, bromine, chloride, or iodine.

Hereinafter, a polymeric compound, an oxygen permeable membrane, and an electrochemical device according to embodiments will be described in greater detail. The non-limiting descriptions given below are for illustrative purposes only, and the present invention is only defined by the scope of the claims below.

1. Polymeric Compound

According to an aspect, provided is a polymeric compound including a cross-linked backbone which is a reaction product of a multifunctional acrylate compound and a metal porphyrin derivative, wherein the metal porphyrin derivative has a first axial position and a second axial position, and includes a basic coordination ligand coordinated at the first axial position (position 5) of the metal porphyrin derivative. The metal porphyrin derivative may further include an oxygen molecule coordinated at the second axial position (position 6), which is opposite to the first axial position (position 5) of the metal porphyrin derivative. The basic coordination ligand may include a nitrogen-containing organic ligand. The basic coordination ligand will be described in more detail below.

The polymeric compound includes the cross-linked backbone including a reaction product of the multifunctional acrylate compound and the metal porphyrin derivative, such that even when the amount of the metal porphyrin in the polymeric compound is large, oxygen selective permeability may be maintained without decreasing workability and free-standing property of the membrane.

Also, the basic coordination ligand binds to position 5 of the central metal of the metal porphyrin derivative to facilitate coordination of an oxygen molecule at position 6 thereof, thereby improving the selective oxygen permeability of the polymeric compound including the metal porphyrin derivative, even at a pressure difference that is equal to or greater than the oxygen partial pressure in the air.

1.1. Structure of Polymeric Compounds

Figure 1B:
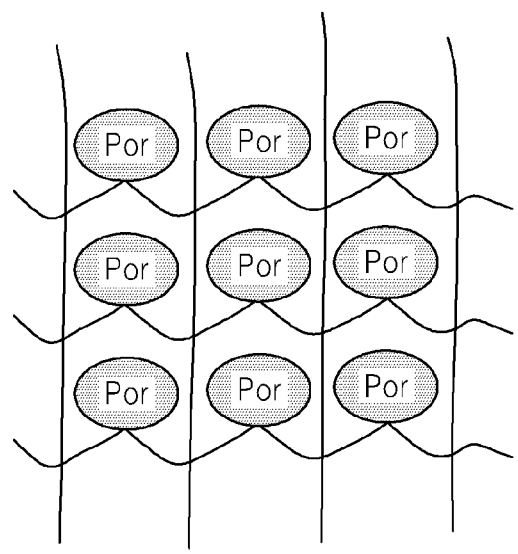
FIG. 1B is a conceptual diagram illustrating a structure of a polymeric compound according to another embodiment.

A structure of the polymeric compounds will be described with reference to FIG. 1. FIG. 1A is a conceptual diagram illustrating a structure of a polymeric compound according to an embodiment. FIG. 1B is a conceptual diagram illustrating a structure of a polymeric compound according to another embodiment. Hereinafter, the expression "acrylate compound" as used herein also refers to "a (meth)acrylate compound", unless stated otherwise.

The polymeric compound may include a cross-linked backbone which is a reaction product of the multifunctional acrylate compound and the metal porphyrin derivative, i.e., in which the multifunctional acrylate compound and the metal porphyrin are bound one another.

In particular, the metal porphyrin derivative includes at least one nucleophilic functional group, wherein the at least one nucleophilic group is bound to an acryl group included in the multifunctional acrylate compound to form a cross-linked backbone by a Michael-type addition reaction. A functional group derived from the metal porphyrin derivative may be included in a main chain or a pendant group of the cross-linked backbone.

The metal porphyrin derivative may be a metal porphyrin complex. For example, the metal porphyrin complex may be a cobalt porphyrin complex. Hence, the cobalt porphyrin complex may bind to the multifunctional acrylate compound, the product of which binds to another multifunctional acrylate compound to form a backbone of the polymeric compound. A portion derived from the cobalt porphyrin complex may be included in the main chain or the pendant group of the cross-linked backbone. The binding of the basic coordination ligand to position 5 of cobalt of the cobalt porphyrin complex facilitates coordination of an oxygen molecule at position 6 thereof, and thus, the permeation of oxygen may be accelerated even when the pressure difference before and after the formation of the membrane is greater than the oxygen partial pressure in the air. As a result, electrochemical devices using the air as a positive active material, such as air batteries, may have improved electrochemical properties.

An amount of the metal porphyrin derivative may be 30 percent by weight ("weight %") or greater based on the weight of the polymeric compound.

Multifunctional Acrylate Compound

A multifunctional acrylate compound has two or more acryl groups and may be a Michael acceptor in a Michael-type addition reaction. In a monofunctional acrylate compound, the monofunctional acrylate compound may not form a polymer structure with a metal porphyrin derivative described below, such as a cobalt porphyrin complex.

The multifunctional acrylate compound may include, for example, a bifunctional acrylate formed of a reactive monomer such as neopentyl glycol diacrylate and dipropylene acryl diacrylate, and a reactive oligomer such as polyethylene glycol acrylate, urethane acrylate, and epoxy acrylate; a trifunctional acrylate formed of a reactive monomer and a reactive oligomer, such as trimethylolpropane triacrylate and pentaerythritol triacrylate, and an acrylate having four or more functional groups, formed of a reactive monomer and a reactive oligomer, such as pentaerythritol tetraacrylate and dipentaerythritol hexaacrylate.

Among the multifunctional acrylate compounds, the multifunctional acrylate compound may be a monomeric acrylate compound having 20 or less carbon atoms. The monomeric acrylate compound may be, for example, a diacrylate represented by Formula 2, a triacrylate represented by Formula 3, and a tetraacrylate represented by Formula 4. Due to the use of the monomeric acrylate compound, the amount of the metal porphyrin derivative, such as the cobalt porphyrin complex, per one molecule of the polymeric compound may be increased.

Formula 2

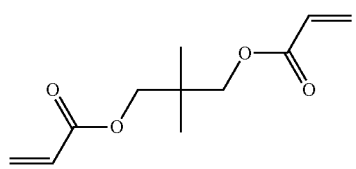

Formula 3

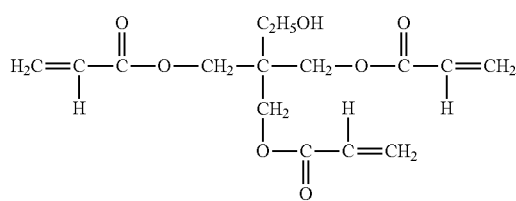

Formula 4

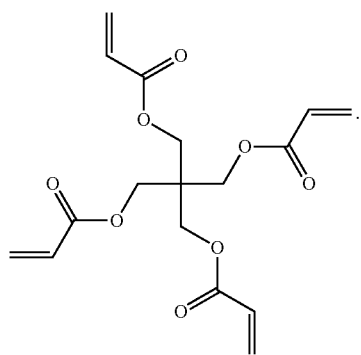

The above-listed bifunctional or multifunctional acrylates may be used alone or as a combination of at least two of the foregoing acrylates as the multifunctional acrylate compound. The above-listed bifunctional acrylates and multifunctional acrylates may be synthesized for use according to known methods, or may be commercially available.

Also, the multifunctional acrylate compound may include a halogen-substituted alkylene group. A polymeric compound synthesized by using the multifunctional acrylate compound and the metal porphyrin derivative, such as the cobalt porphyrin complex, may have water repellency. Non-limiting examples of the multifunctional acrylate compound having the halogen-substituted alkylene group may be, for example, diacrylate represented by Formula 5.

Formula 5

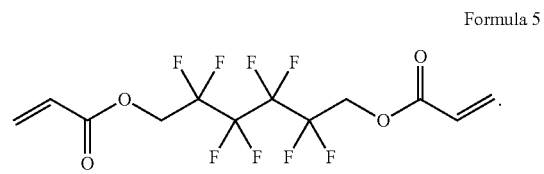 [SMILES: C=CC(=O)OCC(F)(F)C(F)(F)C(F)(F)C(F)(F)COC(=O)C=C]

Metal Porphyrin Derivative

The metal porphyrin derivative may be a complex in which a metal is coordinated to a tetraphenyl porphyrin derivative represented by Formula 1 below:

Formula 1

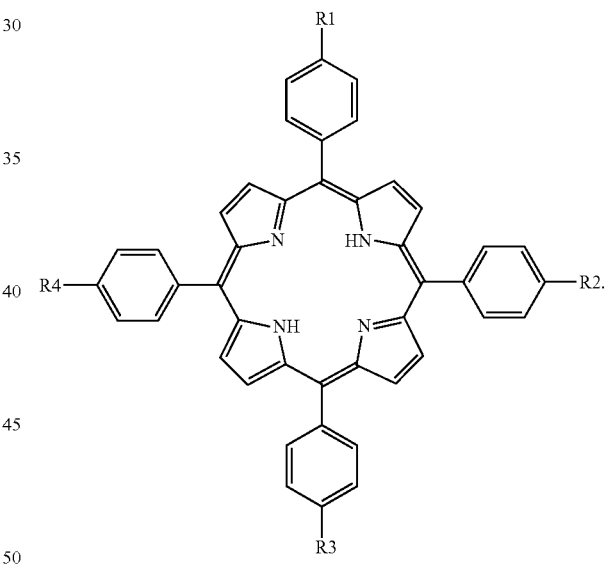

In Formula 1 above,

R1, R2, R3, and R4 are each independently an amino group, an acetoacetate group ($CH_3C(=O)CH_2C(=O)O—$), an acetoacetamide group ($CH_3C(=O)CH_2C(=O)NH—$), a cyanoacetate group ($NCCH_2C(=O)O—$), a cyanoacetamide group ($NCCH_2C(=O)NH—$), hydrogen, a halogen group, a substituted or unsubstituted C1-C10 alkyl group, a substituted or unsubstituted C2-C10 alkenyl group, a substituted or unsubstituted C2-C10 alkynyl group, a substituted or unsubstituted C6-C10 aryl group, or a combination thereof, with the proviso that at least one of R1, R2, R3, and R4 may include a group selected from an amino group, an acetoacetate group, an acetoacetamide group, a cyanoacetate group, and a cyanoacetamide group.

The metal porphyrin derivative may be, for example, the cobalt porphyrin complex. In greater detail, the metal porphyrin derivative may be a complex in which cobalt is coordinated to the tetraphenyl porphyrin derivative represented by Formula 1 above.

In this regard, in Formula 1 above, R1, R2, R3, and R4 are nucleophilic functional groups, or in other words, functional groups that may be Michael donors. The "Michael donors" as used herein refer to functional groups that may be Michael donors in a Michael-type addition reaction.

The nucleophilic functional group may be a functional group including a nitrogen atom or an oxygen atom with an unshared electron pair. Non-limiting examples of the nucleophilic functional group are an amino group, an acetoacetate group, an acetoacetamide group, a cyanoacetate group, and a cyanoacetamide group. Among the nucleophilic functional groups, an amino group or an acetoacetate group may be used, but the solubility of a porphyrin cobalt complex having an amino group in a cast solution is reduced, thereby causing difficulties in forming a membrane. Accordingly, when the polymeric compound is used for an oxygen permeable membrane, the acetoacetate group is preferred to the amino group.

Also, in Formula 1, R1, R2, R3, and R4, may be other than the nucleophilic functional groups, for example, substituents with a small molecular weight, without a reduction in the amount of the cobalt porphyrin complex in the polymeric compound. Examples of such residues are hydrogen, a halogen group, a C1-C10 alkyl group, a C2-C10 alkenyl group, a C2-C10 alkynyl group, and a substituted or unsubstituted C6-C10 aryl group.

The term "substitution" as used herein refers to a substitution with a halogen atom, a C1-C10 alkyl group substituted with a halogen atom, e.g., $CCF_3$, $CHCF_2$, $CH_2F$, and $CCl_3$), a hydroxy group, a nitro group, a cyano group, an amino group, an amidino group, hydrazine, hydrazone, a carboxyl group or a salt thereof, a sulfonic acid or a salt thereof, a phosphoric acid or a salt thereof, a C1-C10 alkyl group, a C2-C10 alkenyl group, a C2-C10 alkynyl group, a C1-C10 heteroalkyl group, a C6-C10 aryl group, a C6-C10 arylalkyl group, a C6-C10 heteroaryl group, or a C6-C10 heteroarylalkyl group.

In this regard, when the multifunctional acrylate compound only includes the monofunctional acrylate, the tetraphenyl porphyrin derivative only includes one nucleophilic functional group. In other words, when only one of R1 to R4 of Formula 1 is a nucleophilic functional group, the cobalt porphyrin complex and the multifunctional acrylate compound may not form a cross-linked polymer structure. Accordingly, when the multifunctional acrylate compound only includes the bifunctional acrylate, the tetraphenyl porphyrin derivative may have at least two nucleophilic functional groups.

Meanwhile, when the multifunctional acrylate compound includes at least one type of the multifunctional acrylate of bifunctional group or higher, the cobalt porphyrin complex and the multifunctional acrylate may form the cross-linked polymer structure even when the tetraphenyl porphyrin derivative only has one nucleophilic functional group. Accordingly, when the multifunctional acrylate compound includes at least one type of the multifunctional acrylate of bifunctional acrylate or higher, a tetraphenyl sulpyrine derivative may have at least one nucleophilic functional group.

Basic Coordination Ligand

Due to the coordination of the basic coordination ligand at position 5 of cobalt, which is the core metal of the metal porphyrin complex, an oxygen molecule may be preferentially coordinated at position 6 thereof, which is disposed opposite to position 5 in the axial direction of the cobalt porphyrin complex. As a result, even when a pressure difference before and after the formation of the membrane is greater than the oxygen partial pressure in the air, facilitated transport of oxygen by the cobalt porphyrin complex may occur, which may substantially increase the oxygen selective permeability of the cobalt porphyrin complex.

The basic coordination ligand may be a molecule having a functional group that has high electron donating characteristics due to the presence of an unshared electron pair or the like. The basic coordination ligand may be an amino group, a phosphino group, a carboxy group, a thiol group, or the like.

The basic coordination ligand may include a nitrogen-containing organic ligand. The nitrogen-containing organic ligand may be an amine (such as methylamine, trimethylamine, ether amine, pyridine, hexamethylene diamine, morpholine, and aniline), an imine (such as ethylene imine and a Schiff base), and an imidazole (such as methylimidazole, benzylimidazole, and trimethylimidazole).

Also, other basic coordination ligands include triphenylphosphine, acetyl acetate, and ether. An example of the basic coordination ligand is 1-benzyl-1H-imidazole (Blm) represented by the formula below.

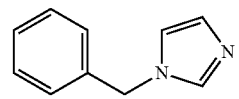 [SMILES: c1ccc(Cn2ccnc2)cc1]

The basic coordination ligand that has high basicity, or in other words, high electron donating characteristics, increases oxygen affinity of the metal porphyrin derivative, for example, the cobalt porphyrin complex. This may occur because when electron donating characteristics are strong, electron mobility from Co to a π* orbit of an oxygen molecule is facilitated, which in turn facilitates the formation of a bond between Co—$O_2$. The electron state of Co—$O_2$ may actually be a polarized state of Co(III)$^+$-$O_2^-$ instead of Co(II)-$O_2$.

Increase in a distance between Co—N due to steric hindrance of the cobalt porphyrin complex and distortion of molecules affects electronic properties of the basic coordination ligand, thereby deteriorating the coordination ability of the basic coordination ligand with respect to the cobalt porphyrin complex. In other words, increase in steric hindrance and distortion cause difficulties for the basic coordination ligand to approach the cobalt porphyrin complex and weakens electric bonding between Co—N (increase in the distance between Co—N), thereby deteriorating the coordination ability of the basic coordination ligand.

The measurement of UV-visible spectrum of the cobalt porphyrin complex represents maximization of a soret band and a Q band. When 5 molar equivalents of the basic coordination ligand (imidazole) with respect to the total amount of cobalt porphyrin complex is added, a peak of the Q band undergoes a long wavelength shift, and thus, it may be concluded that the basic coordination ligand coordinated to the cobalt porphyrin complex. Even under the presence of an excess amount (100 molar equivalents) of the basic coordination ligands in the cobalt porphyrin complex, it may be inferred that almost 100% of the basic coordination ligands coordinated to the cobalt porphyrin complexes, similar to the situation when 5 equivalents of the basic coordination ligands were added, since nothing else was observed in the spectrum.

Also, when the basic coordination ligand is coordinated to the cobalt porphyrin complex and then exposed to oxygen, the soret band and the Q band may undergo a long wavelength shift. Accordingly, the basic coordination ligand coordinates at position 5 of the cobalt porphyrin complex and an oxygen molecule coordinates at position 6 thereof.

Polymeric Compound

A polymeric compound may be obtained through a Michael-type addition reaction between a multifunctional acrylate compound and a metal porphyrin derivative, for example, a cobalt porphyrin complex. In this reaction, some or all of the nucleophilic functional groups of the cobalt porphyrin complex (for example, an amino group or an acetoacetate group) are added to an acryl group of the acrylate compound. A structure of the polymeric compound including a backbone obtained through the Michael-type addition reaction will now be described with reference to FIGS. 1A and 1B. In FIGS. 1A and 1B, "Por" indicates that porphyrin is present in a site represented as "Por", i.e., that porphyrin is present in a site originating from the cobalt porphyrin complex.

Embodiment 1

A polymeric compound according to the first embodiment of the present disclosure may have the structure of FIG. 1A, in which the cobalt porphyrin complex is present in a main chain of the backbone obtained through the Michael-type addition reaction between the multifunctional acrylate compound and the cobalt porphyrin complex. In this regard, the multifunctional acrylate compound and the cobalt porphyrin complex are engaged with and bound by having each other as a medium. That is, the multifunctional acrylate compound (the cobalt porphyrin complex) may bind to each other by having the cobalt porphyrin complex (multifunctional acrylate compound) as a medium.

This structure may be obtained, for example, by adding a tetra-substituted cobalt porphyrin complex having four nucleophilic functional groups to multifunctional acrylates such as a bifunctional acrylate, or trifunctional, tetrafunctional or higher acrylate compound via a Michael-type addition reaction. When the bifunctional acrylate compound and the tetra-substituted cobalt porphyrin complex react, the extent of cross-linkage is low, i.e., the number of cross-linkage points between the bifunctional acrylate compound and the cobalt porphyrin complex is low, which facilitates the dissolution of the polymeric compound in an organic solvent, thereby causing difficulties in the formation of the membrane or weakening the strength of the membrane. When the tetrafunctional acrylate compound and the tetra-substituted cobalt porphyrin complex react, the polymeric compound may be insoluble or barely soluble in the organic solvent. However, in such case, there are too many cross-linkage points, i.e., cross-linkage points between the tetrafunctional acrylate compound and the cobalt porphyrin complex, so the formed membrane tends to be fragile. Accordingly, to form the polymeric compound that is insoluble in the organic solvent as well as to decrease the number of cross-linkage points, a polymeric compound having a structure described in Embodiment 2 below may be used.

Embodiment 2

A polymeric compound according to a second embodiment of the present disclosure may have the structure of FIG. 1B, in which the cobalt porphyrin complex is present in a side chain of the backbone obtained through the Michael-type addition reaction between the multifunctional acrylate compound and the cobalt porphyrin complex. In this regard, when the same type of multifunctional acrylate compounds are polymerized, (or when two or more types of the multifunctional acrylate compounds are used, the compounds are copolymerized) to form polyacrylate in the main chain, and the cobalt porphyrin complex may be bound to a side chain of the polyacrylate.

This structure may be obtained, for example, by subjecting the tetrafunctional acrylate compound and a monosubstituted cobalt porphyrin complex having only one nucleophilic functional group to a Michael-type addition reaction. In this regard, the number of cross-linkage points may be chosen such that the poor solubility in an organic solvent and high brittleness of the membrane are balanced.

Molecular Weight (Polymerization Degree) of Polymeric Compound

A molecular weight (or polymerization degree) of the polymeric compound is not specifically limited and may be appropriately adjusted according to the use of the polymeric compound.

1.2. Synthesis Method of Polymeric Compound

Hereinafter, a method of synthesizing the polymeric compound having the structure described above will be described.

As described above, the polymeric compound may be obtained through a Michael-type addition reaction between a bifunctional or multifunctional acrylate compound and a cobalt porphyrin complex having at least one nucleophilic functional group. In particular, in synthesizing the polymeric compound, the nucleophilic functional group (such as amino group, acetoacetate group, or the like) serving as a Michael donor reacts with an acryl group of the multifunctional acrylate compound serving as a Michael acceptor in the Michael addition reaction, thereby adding the cobalt porphyrin complex to the acrylate compound. This will be described in greater detail below.

Preparation of Multifunctional Acrylate Compound

First, a multifunctional acrylate compound is prepared for the synthesis of the polymeric compound. The multifunctional acrylate compound may be synthesized using a known method or may be a commercially available compound. Examples of the commercially available compound are neopentyl glycol diacrylate (available from Aldrich), pentaerythritol tetraacrylate (available from Aldrich), 1,4-bis(acryloyloxy)butane (available from TCI), 1,10-bis(acryloyloxy)decane (available from TCI), tetraethylene glycol diacrylate (available from TCI), pentaerythritol triacrylate (available from SHIN-NAKAMURA CHEMICAL CO., LTD.), bisphenol-A epoxy acrylate (available from DAICEL-CYTEC COMPANY LTD.), and aliphatic urethane acrylate (available from DAICEL-CYTEC COMPANY LTD.).

Synthesis of Tetraphenylporphyrin Derivative

Tetraphenylporphyrin may be synthesized using a known method, or may be commercially available. Examples of the commercially available tetraphenylporphyrin are tetraphenylporphyrins (available from TCI, Waco Chemicals, Sigma Aldrich, Strem Chemicals, and the like).

Next, a nucleophilic functional group, such as an amino group or an acetoacetate group, is introduced into the tetraphenylporphyrin. The nucleophilic functional group may be introduced via a known organic synthesis reaction. For example, an amino acid group (mono- or tri-substituted) may be introduced as follows:

First, in order to introduce an amino group, for example, as illustrated in Formula 7 (Reaction Scheme 1) below, tetraphenylporphyrin and sodium nitrite are reacted in trifluoroacetic acid to synthesize a tetraphenyl sulpyrine derivative with 1 to 3 nitro groups. Then, the nitro groups are reduced using a reducing agent, such as concentrated hydrochloric acid to synthesize a tetraphenylporphyrin derivative with 1 to 3 amino groups.

Reaction Scheme 1

Formula 7

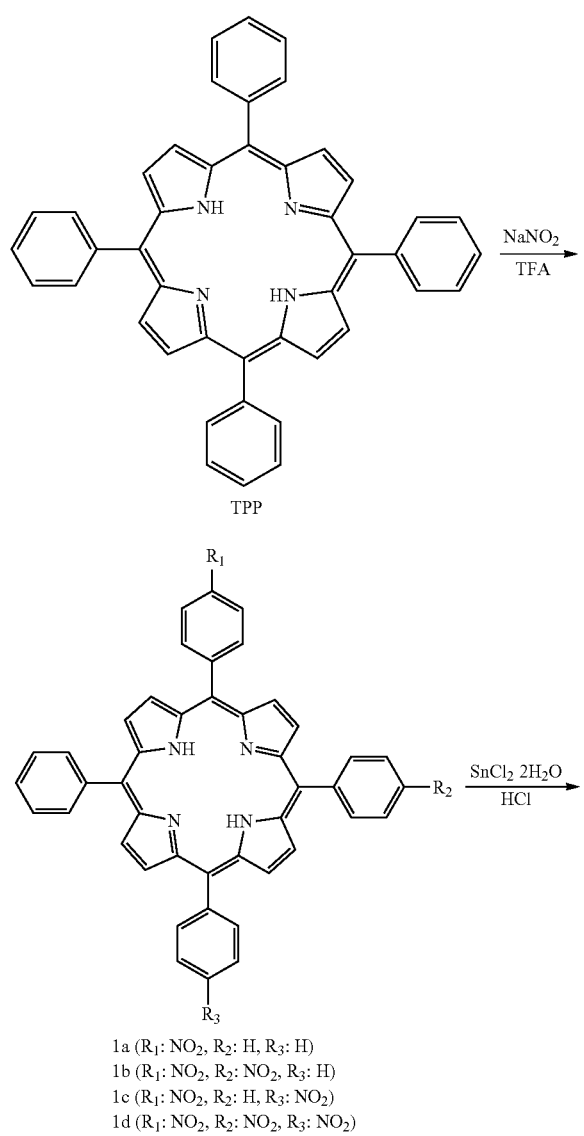

1a ($R_1$: $NO_2$, $R_2$: H, $R_3$: H)
1b ($R_1$: $NO_2$, $R_2$: $NO_2$, $R_3$: H)
1c ($R_1$: $NO_2$, $R_2$: H, $R_3$: $NO_2$)
1d ($R_1$: $NO_2$, $R_2$: $NO_2$, $R_3$: $NO_2$)

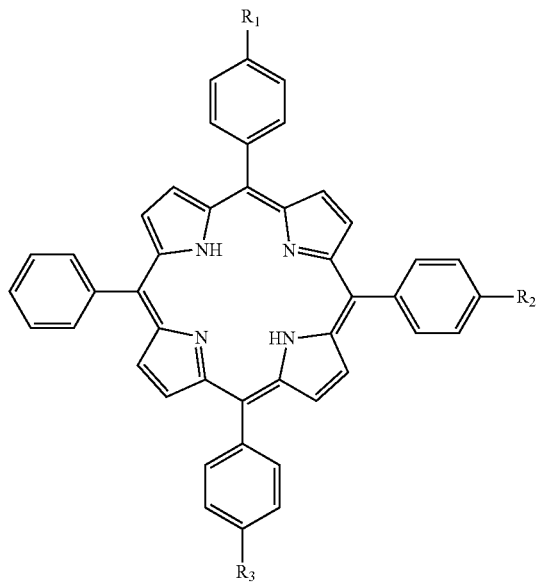

2a ($R_1$: $NH_2$, $R_2$: H, $R_3$: H)
2b ($R_1$: $NH_2$, $R_2$: $NH_2$, $R_3$: H)
2c ($R_1$: $NH_2$, $R_2$: H, $R_3$: $NH_2$)
2d ($R_1$: $NH_2$, $R_2$: $NH_2$, $R_3$: $NH_2$)

Although the tetraphenyl sulpyrine may be synthesized as above for use, any commercially available tetraphenyl sulpyrine derivative may also be used. An example of a commercially available tetraphenylsulpyrine derivative is 5,10,15,20-tetrakis(4-aminophenyl)-21H,23H-porphyrine (available from TCI).

Cobalt Coordination

The tetraphenylporphyrin derivative synthesized as described above may be coordinated to cobalt using a known method, but is not specifically limited. For example, the tetraphenylporphyrin derivative may be dissolved in a mixed solvent of dimethylformamide ("DMF") and chloroform, and then react with cobalt chloride hexahydrate in the presence of rutidine, thereby synthesizing a cobalt porphyrin complex of the tetraphenylporphyrin derivative coordinated to cobalt.

Michael-Type Addition Reaction

Next, the cobalt porphyrin complex synthesized as described above and the acrylate compound are dissolved in a solvent, and a catalyst is added thereto to facilitate a Michael-type addition reaction, to thereby synthesize a polymeric compound.

Examples of the solvent that is available in the present disclosure are acetone, chloroform, benzene, toluene, tetrahydrofuran, ethanol, 2,2,2-trifluoroethanol, and t-butyl acetoacetate.

An appropriate solvent may be selected from the foregoing examples depending on the solubility of the cobalt porphyrin complex and the acrylate compound in the solvent.

Any catalyst selected from a variety of catalysts that are in common use in a Michael-type addition reaction may be used. Examples of the catalyst are amine catalysts, such as diazabicycloundecene ("DBU"), tetramethylethylenediamine, tetramethylalkylenediamine, and N-methyldicyclohexylamine; basic catalysts, such as sodium methoxide, sodium ethoxide, potassium tertiary butoxide, sodium hydroxide, a quaternary ammonium hydroxide, such as tetramethylammonium hydroxide, metallic sodium, and butyl lithium. Examples of organic metal catalysts are ruthenium cyclooctadiene cyclooctatriene, iron acetylacetate, and nickel acetylacetate. For example, a catalyst that does not contain a metal may be used.

Coordination of a Basic Coordination Ligand

Before subjecting the cobalt porphyrin complex and the multifunctional acrylate compound to the Michael-type addition reaction, the cobalt porphyrin complex is dissolved in a solvent, and then a basic coordination ligand such as methyl imidazole or benzyl imidazole is added to the resultant solution, thereby reacting the cobalt porphyrin complex and the basic coordination ligand compound.

1.3. Effect of Polymer Compound

According to the above-described embodiments, the polymeric compound has more cross-linkage points between the cobalt porphyrin complex and the multifunctional acrylate compound, i.e., more cross-linkage points between the nucleophilic functional group of the cobalt porphyrin complex and the acryl group of the multifunctional acrylate compound than existing polymeric compounds. Therefore, the polymeric compound according to the present disclosure may have higher porphyrin content (proportion of the content of the cobalt porphyrin complex per unit amount of the polymeric compound) than existing polymeric compounds. For example, the content of the cobalt porphyrin complex per unit amount of the polymeric compound may be 30 weight % or greater.

In particular, the use of a single acrylate as the multifunctional acrylate compound may result in markedly higher porphyrin content than existing cobalt porphyrin complex containing compounds.

When a fluoro group is introduced into an alkylene chain of the multifunctional acrylate compound, the cobalt porphyrin complex containing polymeric compound may have improved water repellency.

Furthermore, due to the bonding of the basic coordination ligand to position 5 of the cobalt porphyrin complex, an oxygen molecule may be preferentially coordinated at position 6 thereof, which is disposed opposite to position 5 in the axial direction of the cobalt porphyrin complex. Accordingly, facilitated transport of oxygen may occur. This may markedly improve oxygen selective permeability of the cobalt porphyrin complex, even at a pressure greater than the oxygen partial pressure (about 15 centimeters of Hg) in the air. Due to such effects, an electrochemical device that operates by consuming oxygen may enable selective supply of oxygen to the electrochemical device, even when a large amount of current is needed. Simultaneously, oxygen concentration may be increased in the electrochemical device and overvoltage during a redox reaction of oxygen may be reduced.

2. Oxygen Permeable Membrane and Oxygen Permeable Material

Hereinafter, an oxygen permeable membrane and an oxygen permeable material, each using the polymeric compound described above, will be described in greater detail. The oxygen permeable membrane may be formed using the polymer compound. The oxygen permeable membrane is a free-standing membrane with enhanced flexibility, and thus may be used for a variety of uses, for example, as a barrier of an electrochemical device. The polymeric compound has a high porphyrin content, i.e., a high cobalt porphyrin complex content, and also allows selective binding (intercalation/deintercalation) of oxygen molecules to the cobalt porphyrin complex. Thus, the oxygen permeable membrane formed using the polymeric compound may have high oxygen permeability, and allow a large amount of oxygen to selectively pass through the oxygen permeable membrane.

Furthermore, when an acrylate compound having a fluoro group introduced to an alkylene chain is used as a multifunctional acrylate compound, a polymeric compound with improved water repellency may be obtained. Therefore, the oxygen permeable membrane formed using the polymeric compound may have high oxygen permeability and high water repellency, thereby forming a high performance oxygen permeable membrane. In this regard, the unit of the multifunctional acrylate compound with the fluoro group has high oxygen permeability, which thereby facilitates oxygen diffusion into the membrane. Furthermore, due to the water repellency of the oxygen permeable membrane, oxygen inflow into the membrane is unlikely to be blocked by water droplets on the surface of the oxygen permeable membrane. Therefore, the oxygen permeable membrane may be installed, for example, onto an oxygen inlet of an electrochemical device to stably supply oxygen to the electrochemical device.

The oxygen permeable membrane may be formed on a porous substrate or in pores of the porous substrate to form an oxygen permeable composite. Since the oxygen permeable membrane is bound with the porous substrate, water repellency and durability of the oxygen permeable material with the oxygen permeable membrane on the porous substrate may be improved. Therefore, using the oxygen permeable material may ensure more stable oxygen permeability for a long time. For example, the oxygen permeable material may be installed onto an oxygen inlet of an electrochemical device to stably supply oxygen to the electrochemical device for a long time.

Furthermore, since the oxygen permeable membrane has a high cobalt porphyrin complex content (abundance ratio) and the basic coordination ligand is coordinated to the cobalt porphyrin complex, the oxygen permeable membrane may still have higher oxygen permeability than existing oxygen permeable membranes with a low cobalt porphyrin complex content even when the oxygen permeable membrane is formed on the porous substrate or in the pores of the porous substrate.

When the oxygen permeable material is prepared, an acetate-substituted cobalt porphyrin complex, in which the basic coordination ligand is bound to the porous substrate, and a multifunctional acrylate compound solution are coated on a porous substrate by using a bar coater method or the like, the product of which is then subjected to a Michael-type addition reaction to prepare a membrane formed of polymers at a room temperature. In addition to the bar coater method, a spray coater method, a slit coater method, a slit and spin coater method, a spin coater method, and an inkjet method may be used. As the porous substrate, a microporous polymer sheet (formed of polypropylene such as Cell Guard 2400 available from Toray Co. Ltd., or polyethylene) may be selected.

Before the oxygen permeable membrane is coated on the porous substrate, a gas permeable polymer membrane may already have been coated thereon. The gas permeable polymer membrane may be formed from 1-trimethylsilyl propyne to provide poly(1-trimethylsilyl propene) represented by Formula 8. When the gas permeable membrane of poly(1-trimethylsilyl propene) is formed between the oxygen permeable membrane and the porous substrate, the gas permeable membrane may enhance the strength of the oxygen permeable membrane and/or oxygen permeable material without decreasing the oxygen permeability thereof. The gas permeable polymer may be synthesized by the method known in the art described above or may be a commercially available one such as poly(1-trimethylsilyl-1-propene, available from Tokyo Chemical Industry Co., Ltd.)

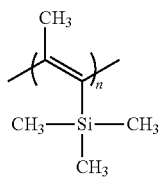

Formula 8

The oxygen permeable membrane has a transmission coefficient of oxygen that is at least 8 times greater than a transmission coefficient of nitrogen thereof when a pressure difference of oxygen before and after the formation of the membrane is 1 cmHg, and at least 2 times greater than a transmission coefficient of nitrogen thereof when a pressure difference of oxygen before and after the formation of the membrane is 50 cmHg.

3. Electrochemical Device

Hereinafter, an electrochemical device using the above-described oxygen permeable membrane or the oxygen permeable material will be described in greater detail. The electrochemical device may use a redox reaction of oxygen. Accordingly, the electrochemical device may be, for example, a metal air battery or a fuel cell. Hereinafter, embodiments of the present disclosure will be described with reference to a metal air battery.

A metal air battery is a rechargeable battery which uses oxygen as a positive active material and a metal as a negative active material. Since oxygen, which is the positive active material, may be obtained from the air, the positive active material may not be charged in the metal air battery, so that a larger proportion of the negative active material may be used in a battery container. Thus, theoretically, the metal air battery may have a higher capacity than secondary batteries using solid positive active material.

In the metal air battery, reaction (A) represented below takes place in the negative electrode. This is an example using lithium as a negative active material.

$$2Li \rightarrow 2Li^+ + 2e^- \quad (A)$$

Electrons generated from reaction formula (A) reach a positive electrode via an external circuit. Lithium ions (Li$^+$) generated from reaction formula (A) migrate by electroosmosis through an electrolyte, which is disposed between the negative electrode and the positive electrode, in a direction from the negative electrode toward the positive electrode.

Reaction formula (B) and (C) represented below take place in a positive electrode.

$$2Li^+ + O_2 + 2e^- \rightarrow Li_2O_2 \quad (B)$$

$$2Li^+ + 1/2 O_2 + 2e^- \rightarrow Li_2O \quad (C)$$

Lithium peroxide (Li$_2$O$_2$) and lithium oxide (Li$_2$O) generated in the positive electrode are accumulated in solid form in the positive electrode (air electrode). During charging, a reverse reaction of reaction formula (A) takes place in the negative electrode, and each of the reverse reactions of reaction formula (B) and (C) takes place in the positive electrode. As a result, metal (lithium) is generated in the negative electrode, enabling redischarging.

The electrochemical device includes a positive electrode using oxygen as a positive active material, a negative electrode using a material that intercalates and deintercalates lithium ions as a negative active material, an electrolyte disposed between the positive electrode and the negative electrode, and a barrier formed of the above-described oxygen permeable membrane, wherein the barrier may be used as a medium for supplying oxygen to the positive electrode.

Figure 2:
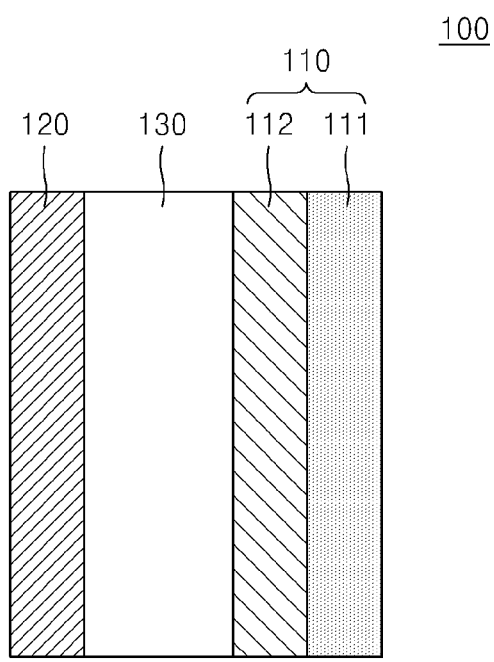
FIG. 2 is a schematic view illustrating a lithium-air battery according to an embodiment.

FIG. 2 is a schematic view illustrating a lithium-air battery 100 according to an embodiment.

Referring to FIG. 2, the lithium air battery 100 includes a positive electrode 110, a negative electrode 120, and an electrolyte 130 disposed between the positive electrode 110 and the negative electrode 120.

The positive electrode 110 includes a current collector 111 and a catalyst layer 112, and uses oxygen as a positive active material. The current collector 111 may act as a porous gas diffusion layer, in which the air may diffuse. The current collector 111 facilitates increases in the surface area to diffuse a large amount of oxygen. The current collector 111 may be anything that has conductivity and is not particularly limited. For example, stainless steel, nickel, aluminum, iron, titanium, carbon, or the like may be used. The current collector 111 of the positive electrode 110 may have a shape of a thin film, sheet, mesh, grid, or the like, and more particularly, the current collector 111 may have a mesh shape. The mesh shape is suitable for the current collector 111 because the mesh shape enables excellent current collection efficiency.

The catalyst layer 112 may include platinum, gold, silver, manganese oxide, iron oxide, or the like and may, for example, include a molecule, in which an electron donor that includes a porphyrin ring as a reduction catalyst, and an electron acceptor, such as a fullerene derivative, are connected by introducing an electro-conductive spacer. The donor may be, for example, a compound having a substituted or unsubstituted porphyrin ring and may, for example, be a porphyrin-metal complex substituted with magnesium (Mg) or nickel (Ni). In this regard, the substituents may be for example, a C1-C10 alkyl group, a C1-C10 alkynyl group, or a C6-C10 aryl group. The acceptor may be, for example, a derivative having a fullerene structure such as C60, C70, C74, and C76 fullerene, and the electro-conductive spacer may, for example, be a condensed nitrogen-containing heterocyclic compound or a hydrocarbon ring. However, in addition to the above-described catalyst, any catalyst that may be used as a catalyst layer of the positive electrode that uses oxygen as a positive electrode material may be used.

The positive electrode 110 may include suitable amounts of a conductor, a binder, a dispersing agent, and a thickener. The conductor may be any electro-conductive material that does not deteriorate electrochemical properties of the electrochemical device according to an embodiment of the present invention. More particularly, examples of the conductor include natural graphite, carbon black, ketjen black, carbon fiber, or the like. The conductor may be used alone or may be used in combination. The binder may be any material that enables bonding of the active material and the conductor. In greater detail, the binder may be polytetrafluoroethylene; a fluoride resin, such as polyvinylidene fluoride; and a thermoplastic resin, such as polypropylene. The amount of the binder is not particularly limited, for example, the amount may be 30 weight % or less, or for example, about 1 weight % to about 10 weight %.

The negative electrode 120 includes a current collector (now shown) and a negative active material.

The current collector of the negative electrode 120 is not particularly limited and may be anything that has conductivity. For example, the current collector may be copper, stainless steel, nickel, or the like. The current collector of the negative electrode 120 may have a shape of a thin film, sheet, mesh, grid, or the like.

The negative active material may include any material that intercalates and deintercalates lithium ions of lithium, lithium oxide, and lithium alloy. For example, the negative active material may include a lithium metal.

The negative electrode 120 may include suitable amounts of a conductor, a binder, a dispersing agent, and a thickener. The types and the amounts of the conductor, the binder, the dispersing agent, and the thickener may be the same as the positive electrode 110.

The positive electrode 110 and the negative electrode 120 may be mixed and dispersed in a suitable solvent to form a positive electrode material and a negative electrode material in a paste form. In addition to the positive active material and the negative active material, a conductor, a binder, or the like may be added to the positive electrode material and the negative electrode material. The positive electrode material and the negative electrode material obtained may be respectively coated on a surface of the current collector to form a positive electrode material and a negative electrode layer.

The electrolyte 130 may conduct metal ions (for example, lithium ions) of the negative active material, and any aqueous electrolyte, non-aqueous electrolyte, or polymer gel electrolyte may be used without limitation, as long as the material enables the dissolution of an oxygen intercalating/deintercalating material described above.

The electrolyte 130 may be a non-aqueous electrolyte.

The solvent of the non-aqueous electrolyte may be an organic solvent known in the art and examples include a cyclic carbonate such as ethylene carbonate, propylene carbonate, butylene carbonate, and vinylene carbonate; a chain carbonate such as diethyl carbonate, dimethyl carbonate, and ethyl methyl carbonate; a cyclic ester carbonate such as gamma-butyrolactone and gamma-valerolactone; a cyclic ether such as tetrahydrofuran and 2-methyl-tetrahydrofuran; a chain ether such as dimethoxyethane and ethylene glycol dimethyl ether; and chloro-ethylene carbonate, fluoroethylene carbonate, 3-methoxy propionitrile, trimethyl phosphate, triphenyl phosphate, sulfolane, and dimethyl sulfoxide.

Also, an ionic solution such as N,N-diethyl-N-ethyl-N-(2-methoxyethyl)ammonium bis(trifluorosulfonyl)imide, N-methyl-N-propylpiperidinium bis(trifluorosulfonyl) imide, 1-methyl-3-propylimidazolium bis(trifluorosulfonyl) imide, and 1-ethyl-3-butylimidazolium tetrafluoroborate may be used. The solvent may be used alone or as a combination of two or more of the foregoing solvents.

The electrolyte may further include a supporting salt. The supporting salt may be dissolved in the above-described solvent to be used as a supply source of lithium ions in a battery. Examples of the supporting salt include hexafluorophosphate ($LiPF_6$), perchlorate ($LiClO_4$), tetrafluoroborate ($LiBF_4$), pentafluoroarsenate ($LiAsF_6$), bis(trifluoromethane sulfonyl) imide ($Li(CF_3SO_2)_2N$), bis(pentafluoroethane sulfonyl)imide ($LiN(C_2F_6SO_2)_2$), trifluoromethane sulfonate ($LiCF_3SO_3$)), and nonafluorobutane sulfonate ($Li(C_4F_9SO_3)$). The supporting salt may be used alone or as a combination of two or more of these.

However, considering that an oxygen molecule may coordinate at position 6 of the tetraphenyl porphyrin complex, the supporting salt may be selected in accordance with the type of the basic coordination ligand added.

Meanwhile, the electrochemical device uses oxygen as a positive active material and accordingly, when the oxygen is externally supplied, it becomes important to efficiently supply a gas having high oxygen partial pressure into the electrochemical device. Because the air may diffuse into the positive electrode from the outside, the above-described oxygen permeable membrane or the barrier formed of an oxygen permeable material may be disposed at the air inlet, and oxygen may be supplied by using the barrier, i.e., the oxygen permeable membrane or the barrier formed of an oxygen permeable material, as a medium.

The oxygen permeable membrane or the oxygen permeable material positioned at the air inlet includes a large amount of the cobalt porphyrin complex, which may selectively bind to oxygen, and the cobalt porphyrin complex becomes a polymeric compound having markedly improved oxygen selective diffusion depending on the coordination of the basic coordination ligand with the cobalt, and thus, a large amount of oxygen may be selectively diffused. The oxygen permeable membrane or the oxygen permeable material may be positioned at the air inlet of the battery to stably supply the gas having high oxygen partial pressure into the electrochemical device Accordingly, the electrochemical device may show good electrochemical properties. Also, the oxygen permeable membrane or the oxygen permeable material may be used as a barrier on the side of the air inlet of the electrochemical device, such that oxygen concentration of the air supplied into the electrochemical device may be increased and that an overvoltage of the redox reaction may be reduced (ideally, in a second electron reaction, when the oxygen concentration in the air is 21% and a shift factor under the temperature of 25 degrees Centigrade ("° C.") is 0.5, at least 40 millivolts ("mV") of overvoltage is expected, but due to a complex activation process, the actual overvoltage is greater).

Hereinafter, embodiments of the present invention are described in more detail with reference to Examples, but the embodiments of the present invention are not limited to the Examples.

EXAMPLE

Manufacture and Evaluation of Oxygen Permeable Material

First, oxygen permeable membranes were manufactured in the following manners:

Example 1

Manufacture of Oxygen Permeable Membranes

A polymeric compound was synthesized by a Michael-type addition reaction with tetraphenylporphyrin ("TPP") having one acetoacetate group and coordinated to cobalt as a cobalt porphyrin complex, and a tetrafunctional acrylate as an acrylate compound.

In particular, first, a monomer (acetoacetate-substituted porphyrin) with the acetoacetate group serving as a Michael donor introduced into TPP was synthesized according to Reaction Scheme 2 below of Formula 9.

100 milligrams ("mg") (0.15 millimoles ("mmol")) of 5-(4-methoxycarbonylphenyl)-10,15,20-triphenylporphyrin was dissolved in a mixed solvent of DMF/chloroform, followed by an addition of a small amount of rutidine and then 141 mg (0.6 mmol, eq) of cobalt chloride hexahydrate to obtain a mixture, which was then stirred in a nitrogen atmosphere at about 50° C. for about 12 hours, followed by reprecipitation for purification to obtain powder 2(Co) in purple (77 mg, Yield: 70%). Peaks of Q bands in the UV spectrum of the powder 2(Co) were reduced from 4 to 2, representing a metal complex itself, and indicating the incorporation of cobalt. 50 mg (0.068 mmol) of Cobalt porphyrin 2(Co) and 5.2 mg (0.14 mmol) of lithium aluminum hydroxide were dissolved in THF and stirred at room temperature in a nitrogen atmosphere for about 1 hour, followed by column purification to obtain Powder 3(Co) in purple (25.8 mg, Yield: 59%). After dissolving 23 mg (0.033 mmol) of powder 3(Co) in toluene, 4.2 mg, (0.045 mmol, 1.5 eq) of diketene and TEA were added thereto, and stirred at room temperature overnight, followed by column purification to obtain reddish purple powder 1(Co) (8.3 mg, Yield: 27%) as a cobalt porphyrin complex introduced with an acetoacetate group (acetoacetate-substituted cobalt porphyrin).

Reaction Scheme 2

Formula 9

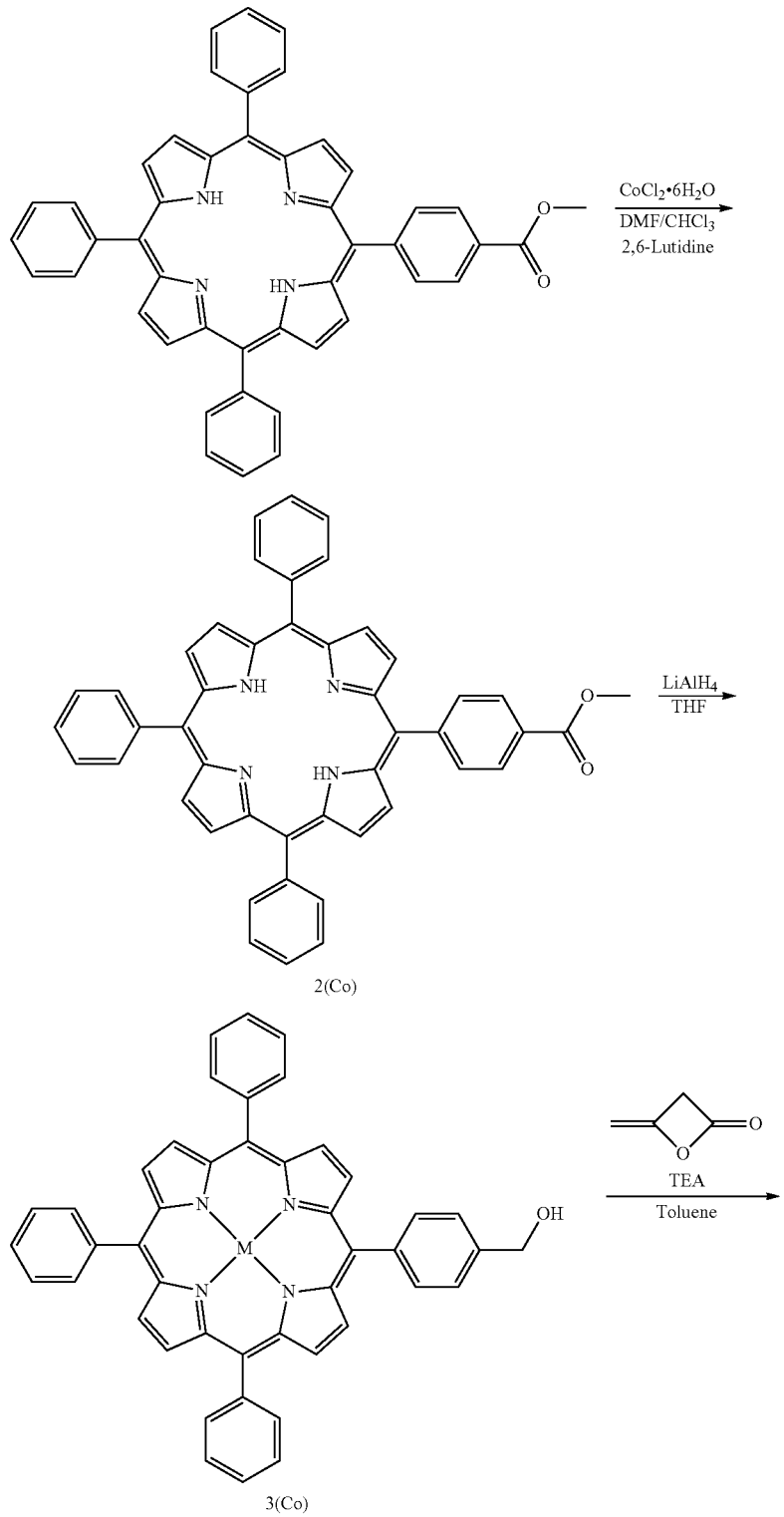

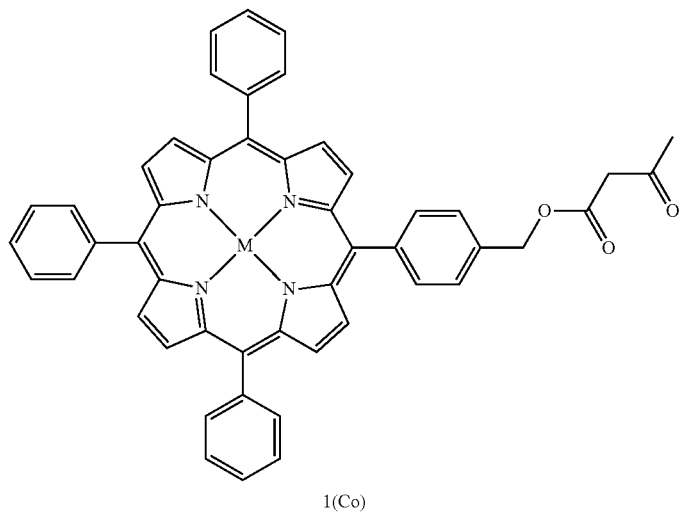

1(Co)

This synthesized cobalt porphyrin complex was subjected to a Michael-type addition reaction to manufacture an oxygen permeable membrane, including the cobalt porphyrin complex.

To enhance the mechanical strength of the oxygen permeable membrane, the oxygen permeable membrane, including the cobalt porphyrin complex, was manufactured on a support membrane. As the support membrane, a polypropylene membrane (Cell Guard #2400, #3501) that is a gas permeable and insoluble in a solvent used in forming the oxygen permeable membrane was used. In particular, poly(1-trimethylsilyl-1-propene) was dissolved in toluene at a concentration of 14 grams per liter ("g/L"), which was then sufficiently stirred and completely dissolved to be coated on the supporting membrane (Cell Guard #2400) by a bar coater method, and then dried for 24 hours. Further, 5 mg (1 molar equivalent) of the acetoacetate-substituted cobalt porphyrin 1(Co) was dissolved in 0.25 milliliters ("ml") of chloroform and then 2 molar equivalents of methyl imidazole or benzyl imidazole was added thereto, which was then sufficiently stirred. After stirring, 1.25 molar equivalents of tetrafunctional acrylate and 1.5 molar equivalents of 1,8-diazabicyclo(5,4,0)-undecene ("DBU") as a catalyst were added in the amount of 20 weight % with respect to porphyrin 1(Co), which was dissolved in chloroform to form a membrane on the poly(1-trimethylsilyl-1-propene) on the support membrane by using a bar coater method at a room temperature, which was then dried for a day and cured, thereby manufacturing the oxygen permeable membrane.

Figure 3:
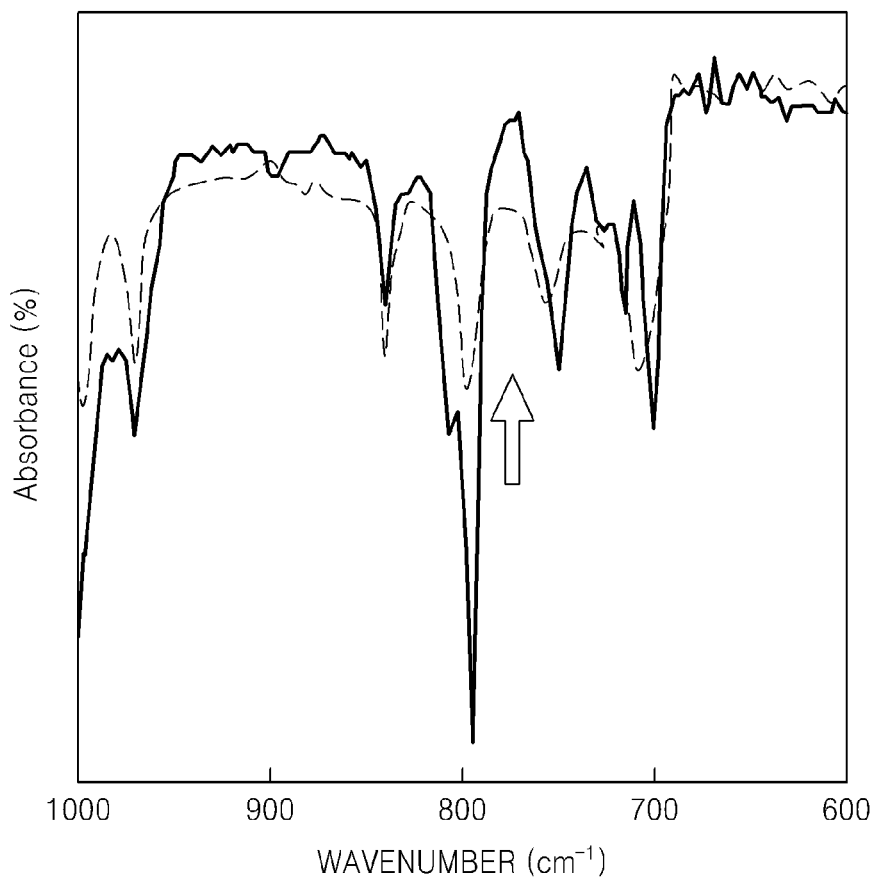
FIG. 3 is a graph of absorbance (percent, %) versus wavenumber (reverse centimeter, $cm^{-1}$), which is a spectra showing infrared ("IR") measurement results before and after curing the oxygen permeable membrane of Example 1.

As a result of infrared ("IR") spectroscopy before and after the curing process, as shown in FIG. 3 (the IR spectra before and after the curing are denoted by solid lines and dashed lines, respectively), an absorption band near 790 reverse centimeters ("$cm^{-1}$") originating from C=C deformation vibration was found to be smaller, indicating that intensity has been reduced and thus, indicating that the acetoacetate-substituted cobalt porphyrin 1(Co) was formed on the support membrane through the Michael-type addition reaction. A reaction conversion rate of the acryl group calculated from the area of the absorption band peak near 790 $cm^{-1}$ was about 76%. A maximum porphyrin content in the cobalt porphyrin complex is about 70 weight %.

Comparative Example 1

Manufacturing Oxygen Permeable Membrane

As a cobalt porphyrin complex, a complex in which cobalt is coordinated to tetraphenylporphyrin having one acetoacetate group was used and as a basic coordination ligand for the complex, a tetrafunctional acrylate was used as an acrylate compound to synthesize a polymer compound through a Michael-type addition reaction.

In particular, first, as shown in Reaction Scheme 2 of Formula 9 below, a monomer (acetoacetate-substituted porphyrin), in which the acetoacetate group acting as a Michael donor was introduced to tetraphenylporphyrin, was synthesized.

100 mg (0.15 mmol) of 5-(4-methoxycarbonylphenyl)-10,15,20-triphenylporphyrin was dissolved in a mixed solvent of DMF/chloroform, followed by an addition of a small amount of rutidine and then 141 mg (0.6 mmol, eq) of cobalt chloride hexahydrate was added thereto to obtain a mixture, which was then stirred in a nitrogen atmosphere at about 50° C. for about 12 hours, followed by reprecipitation for purification to obtain 77 mg of powder 2(Co) in purple (Yield: 70%). Q band peaks in the UV spectrum of the powder 2(Co) were reduced from 4 to 2 representing a metal complex itself, and indicating the incorporation of cobalt. 50 mg (0.068 mmol) of Cobalt porphyrin 2(Co) and 5.2 mg (0.14 mmol) of lithium aluminum hydroxide were dissolved in THF and stirred at room temperature in nitrogen atmosphere for about 1 hour, followed by column purification to obtain 25.8 mg of powder 3(Co) in purple (Yield: 59%). After dissolving 23 mg (0.033 mmol) of powder 3(Co) in toluene, 4.2 mg (0.045 mmol, 1.5 eq) of diketene and TEA were added thereto, and stirred at room temperature overnight, followed by column purification to obtain 8.3 mg of reddish purple powder 1(Co) (Yield: 27%) as a cobalt porphyrin complex with an acetoacetate group (acetoacetate-substituted cobalt porphyrin).

Reaction Scheme 2

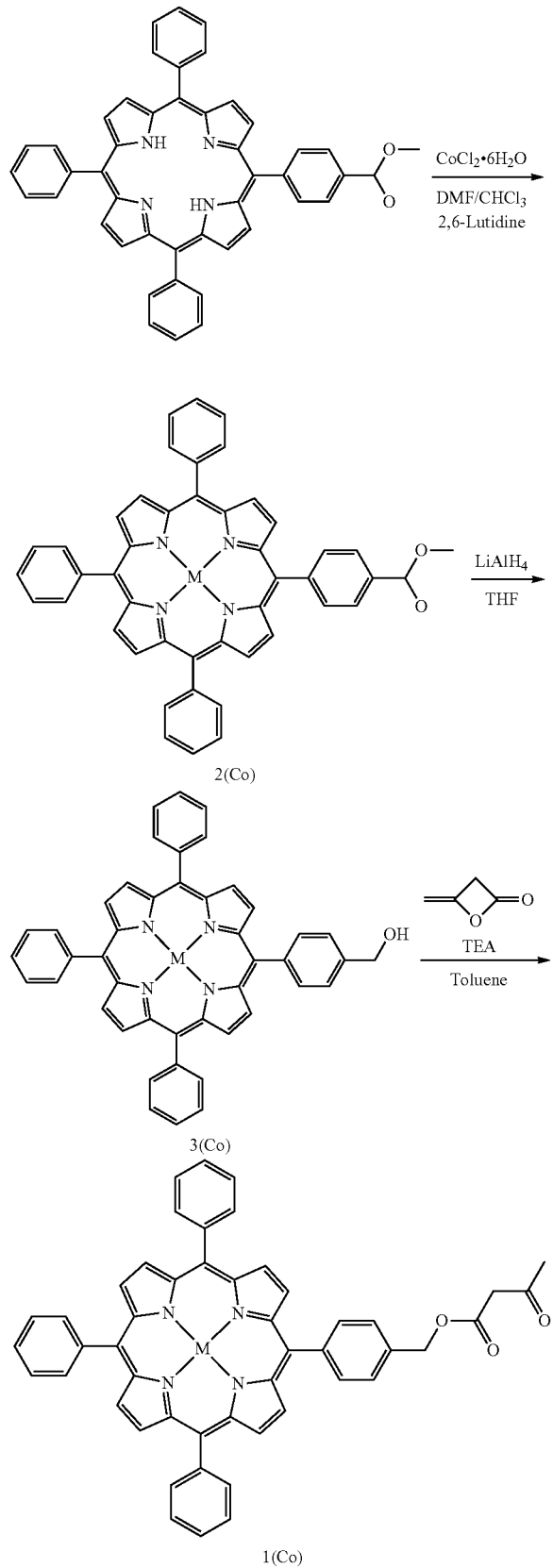

This synthesized cobalt porphyrin complex was subjected to a Michael-type addition reaction to manufacture an oxygen permeable membrane, including the cobalt porphyrin complex. To enhance the mechanical strength of the oxygen permeable membrane, the oxygen permeable membrane, including the cobalt porphyrin complex, was manufactured on a support membrane. As the support membrane, a polypropylene membrane (Cell Guard #2400, #3501) that is a gas permeable and insoluble in a solvent used in forming the oxygen permeable membrane was used. In particular, poly(1-trimethylsilyl-1-propene) was dissolved in toluene at a concentration of 14 g/L, which was then sufficiently stirred and completely dissolved to be coated on the supporting membrane (Cell Guard #2400) by a bar coater method, which was then dried for 24 hours. Further, 5 mg (1 molar equivalent) of the acetoacetate-substituted cobalt porphyrin 1(Co) was dissolved in 0.25 ml of chloroform and then sufficiently stirred. After stirring, 1.25 molar equivalents of tetrafunctional acrylate and 1.5 molar equivalents of t-butylacetoacetate and 1,8-diazabicyclo(5,4,0)-undecene ("DBU") as a catalyst were added in the amount of 20 weight % with respect to porphyrin 1(Co), which was then dissolved in chloroform to form a membrane on the poly(1-trimethylsilyl-1-propene) on the support membrane by using a bar coater method, thereby manufacturing the oxygen permeable membrane.

Example 2

Manufacturing Oxygen Permeable Material

An oxygen permeable material with the oxygen permeable membrane of Example 1 formed on a porous substrate was manufactured. In particular, a hydrophilic polypropylene membrane (Cell Guard #2400 having a thickness of 25 micrometers ("μm") and a pore diameter of 0.125 μm×0.05 μm; Cell Guard #3051 having a thickness of 25 μm) was selected as the porous substrate (porous support membrane). The polypropylene membrane does not diffuse water that passed through gas and thus, a porphyrin solution may be uniformly coated on the support membrane, regardless of the molar concentration of the chloroform solution. As illustrated in Reaction Scheme 3, mg of the acetoacetate-substituted cobalt porphyrin 1(Co)(Mw: 785.8, 10 mg), 2.5 mg (Mw: 352.4, 0.5 eq.) of tetrafunctional acrylate 2, and 1 weight % of DBU were dissolved in 0.2 mL of chloroform to obtain a mixture, which was then coated on a porous support membrane (6 cm×6 cm) using a bar coater method to form a membrane, followed by curing the membrane at room temperature for about 12 hours to obtain an oxygen permeable membrane. No delamination of the oxygen permeable membrane from the porous support membrane occurred even after the curing. As a result, the oxygen permeable material with the oxygen permeable membrane containing about 80 weight % of the cobalt porphyrin complex on the permeable support membrane was obtained.

Comparative Example 2

Manufacturing Oxygen Permeable Material

An oxygen permeable composite was manufactured in the same manner as in Example 2, except that the oxygen permeable membrane of Example 2 was used instead of the oxygen permeable membrane of Example 1.

Evaluation of Oxygen Permeability

A gas permeability coefficient P may be represented as a product of multiplying a diffusion coefficient D by a solubility coefficient S. The gas permeability coefficient P may be determined as a characteristic value independent from the membrane area or thickness, based on Equation 1 below. Equation 1 below is defined using a permeable flow rate Q [cubic centimeters, cm³], a diffusion coefficient D [square centimeters per second "cm² s⁻¹"], a solubility product S [cm³ ("STP") cm⁻³ cmHg], a membrane thickness 1 [cm], a cross-sectional area A [cm²], and a pressure difference p [cmHg].

$$Q = \frac{DSA(p_1 - p_2)}{l} = \frac{PA(p_1 - p_2)}{l} \quad \text{Equation 1}$$

$$P = \frac{Q \times l}{A(p_1 - p_2)} = \frac{Q \times l}{A \Delta p}$$

The oxygen permeable membranes of Example 1 and Comparative Example 1 were tested according to a pressurization method using a beam flux meter ("BFM"), which allows gas (oxygen and nitrogen) to diffuse into the oxygen permeable membrane by applying pressure on the top of the oxygen permeable membrane, and calculates the time it takes for the gas to diffuse into a unit volume of the oxygen permeable membrane. This method may measure a permeable amount of pure gas, and thus may measure the permeable amount of a thin membrane, a membrane that has been weakened by a high concentration of complex support, or a glass polymer membrane or the like casted on a supporter membrane. The method may also measure the permeable flow rate even with a very small sample quantity unlike other methods (such as a low vacuum method or an electrode method) and thus, it takes a short time to measure.

Figure 4A:
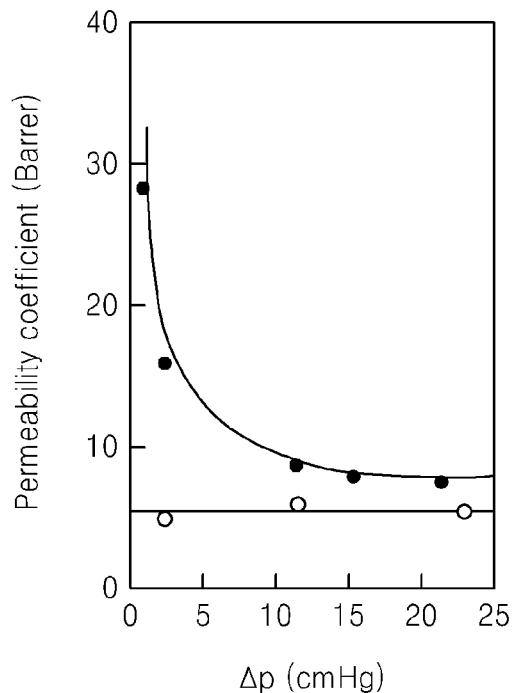
FIG. 4A is a graph of permeability coefficient (Barrer) versus pressure difference (centimeters of mercury, cmHg), which is a characteristic view showing a relationship between a pressure difference ($\Delta p$, $p_1$-$p_2$: horizontal axis) of oxygen and nitrogen and permeability coefficients of oxygen and nitrogen (P: vertical axis) of the oxygen permeable membrane of Comparative Example 1.
Figure 4B:
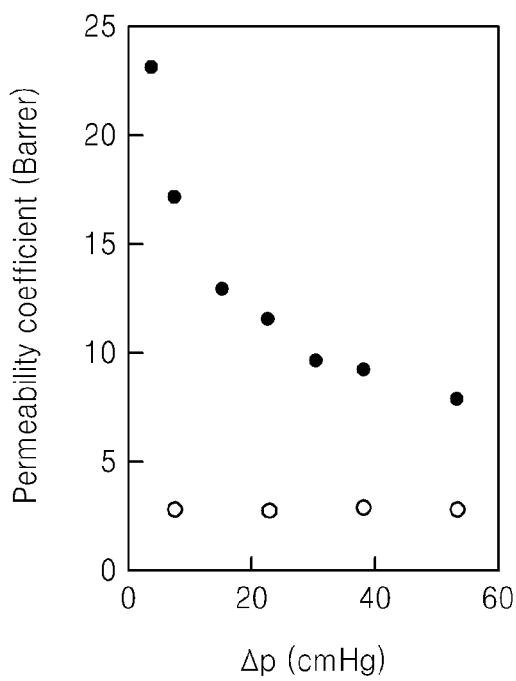
FIG. 4B a graph of permeability coefficient (Barrer) versus pressure difference (centimeters of mercury, cmHg), which shows a relationship between a pressure difference ($\Delta p$, $p_1$-$p_2$: horizontal axis) of oxygen and nitrogen and permeability coefficient of oxygen (P: vertical axis) of the oxygen permeable membrane of Example 1.

FIG. 4A is a characteristic view showing a relationship between a pressure difference ($p_1$-$p_2$: horizontal axis) of oxygen and nitrogen, and permeability coefficients of oxygen and nitrogen (P: vertical axis) of the oxygen permeable membrane of Comparative Example 1 (•: permeability coefficient of oxygen, ○: permeability coefficient of nitrogen). FIG. 4B shows a relationship between a pressure difference (p1-p2: horizontal axis) of oxygen and nitrogen, and permeability coefficient of oxygen (P: vertical axis) of the oxygen permeable membrane of Example 1 (•: permeability coefficient of oxygen, ○: permeability coefficient of nitrogen).

Referring to FIGS. 4A and 4B, depending on the presence or the absence of the basic coordination ligand in the cobalt porphyrin complex, the difference between permeability of oxygen and nitrogen became substantial at a pressure difference of about oxygen partial pressure (about 15 cmHg) in the air. In other words, the difference in permeability between oxygen and nitrogen in the oxygen permeable membrane of Comparative Example 1 is such that oxygen permeability is 1.4 times greater than that of nitrogen while the difference in permeability of oxygen and nitrogen in the oxygen permeable membrane of Example 1 is such that the permeability of oxygen is at least 5 times greater than that of nitrogen. In this regard, depending on the coordination of the basic coordination ligand to the metal porphyrin derivative, oxygen selective permeability may be maintained without any decrease in the oxygen selective permeability even under the pressure difference that is at least as great as the oxygen partial pressure in the air.

As described above, according to the one or more of the above embodiments, provided are a polymeric compound including a metal porphyrin derivative, which may have improved oxygen selective permeability even under the pressure difference of about oxygen partial pressure in the air, an oxygen permeable membrane that uses the polymeric compound, and an electrochemical device having excellent battery performance by using the oxygen permeable membrane.

It should be understood that the exemplary embodiments described therein should be considered in a descriptive sense only and not for purposes of limitation. Descriptions of features or aspects within each embodiment should typically be considered as available for other similar features or aspects in other embodiments.

For example, the above described embodiments are described with reference to an electrochemical device as a metal air battery, but the embodiments are not limited thereto and the electrochemical device described in the embodiments of the present invention may be any battery that uses oxygen in a redox reaction, such as a fuel battery.

Meanwhile, the tetraphenyl porphyrin derivative and a metal porphyrin derivative in which a transition metal, such as copper, is coordinated to the tetraphenylporphyrin derivative, such as a metal porphyrin complex, have oxygen selective permeability, although not as great as the oxygen selective permeability of the cobalt complex.

What is claimed is:

1. A polymeric compound comprising a cross-linked backbone which is a reaction product of a multifunctional acrylate compound and a metal porphyrin derivative, wherein the metal porphyrin derivative comprises a first axial position and a second axial position, and further comprises a basic coordination ligand coordinated at the first axial position of the metal porphyrin derivative, and wherein the metal porphyrin derivative further comprises an oxygen molecule coordinated at the second axial position of the metal porphyrin derivative.

2. The polymeric compound of claim 1, wherein the basic coordination ligand comprises a nitrogen-containing organic ligand.

3. The polymeric compound of claim 1, wherein the reaction product of the multifunctional acrylate compound and the metal porphyrin derivative is a Michael-type addition reaction product.

4. The polymeric compound of claim 1, wherein the metal porphyrin derivative comprises at least one nucleophilic group capable of reacting with an acryl group of the multifunctional acrylate compound to form a Michael-type addition reaction product.

5. The polymeric compound of claim 1, wherein a portion of the metal porphyrin derivative is included in a main chain or a pendant group of the cross-linked backbone.

6. The polymeric compound of claim 1, wherein the metal porphyrin derivative is a complex in which a metal is coordinated to a tetraphenylporphyrin derivative represented by Formula 1:

Formula 1

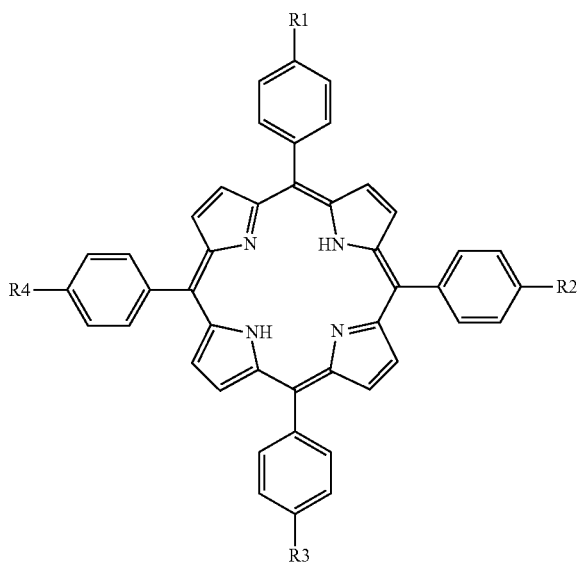

wherein in Formula 1,

R1, R2, R3, and R4 are each independently an acetoacetate group, an acetoacetamide group, a cyanoacetate group, a cyanoacetamide group, hydrogen, a halogen group, a substituted or unsubstituted C1-C10 alkyl group, a substituted or unsubstituted C2-C10 alkenyl group, a substituted or unsubstituted C2-C10 alkynyl group, a substituted or unsubstituted C6-C10 aryl group, or a combination thereof, wherein, at least one of R1, R2, R3, and R4 comprises a group selected from an amino group, an acetoacetate group, an acetoacetamide group, a cyanoacetate group, and a cyanoacetamide group.

7. The polymeric compound of claim 1, wherein an amount of the metal porphyrin derivative is 30 weight % or greater based on a total weight of the polymeric compound.

8. The polymeric compound of claim 1, wherein the multifunctional acrylate compound comprises a bifunctional acrylate, a trifunctional acrylate, a tetrafunctional acrylate, or a combination thereof.

9. The polymeric compound of claim 1, wherein the multifunctional acrylate compound is a acrylate compound comprising 20 or less carbon atoms.

10. The polymeric compound of claim 1, wherein the multifunctional acrylate compound comprises a C1-C10 halogen-substituted alkylene group.

11. An oxygen permeable membrane comprising the polymeric compound according to claim 1.

12. The oxygen permeable membrane of claim 11, wherein the oxygen permeable membrane comprises an oxygen permeable composite membrane disposed on a porous substrate or in pores of the porous substrate.

13. The oxygen permeable membrane of claim 12, wherein the porous substrate comprises a gas permeable polymer membrane disposed thereon.

14. The oxygen permeable membrane of claim 13, wherein the gas permeable polymer membrane comprises poly(1-trimethylsilyl propene).

15. The oxygen permeable membrane of claim 12, wherein a transmission coefficient of oxygen of the oxygen permeable membrane is at least 8 times greater than a transmission coefficient of nitrogen thereof when a pressure difference of oxygen before and after the formation of the membrane is 1 centimeter of mercury, and wherein a transmission coefficient of oxygen of the oxygen permeable membrane is at least 2 times greater than a transmission coefficient of nitrogen thereof when a pressure difference of oxygen before and after the formation of the membrane is 50 centimeters of mercury.

16. An electrochemical device comprising:

a positive electrode using oxygen as a positive active material, a negative electrode using a material that intercalates and deintercalates lithium ions as a negative active material, an electrolyte disposed between the positive electrode and the negative electrode, and a barrier formed of an oxygen permeable membrane comprising the polymeric compound according to claim 1, wherein the barrier is used as a medium for supplying oxygen to the positive electrode.

17. The electrochemical device of claim 16, wherein the reaction product of the multifunctional acrylate compound and the metal porphyrin derivative is a Michael-type addition reaction product.

18. The electrochemical device of claim 16, wherein the electrochemical device is a lithium air battery.

19. The electrochemical device of claim 16, wherein the negative active material is a lithium metal.

* * * * *